(12) United States Patent
Auguet et al.

(10) Patent No.: US 6,872,738 B1
(45) Date of Patent: Mar. 29, 2005

(54) PRODUCT COMPRISING AT LEAST A NO SYNTHASE INHIBITING SUBSTANCE ASSOCIATED WITH AT LEAST A PHOSPHOLIPASE A2 INHIBITING SUBSTANCE

(75) Inventors: Michel Auguet, Palaiseau (FR); Pierre-Etienne Chabrier de Lassauniere, Paris (FR)

(73) Assignee: Societe de Conseils de Recherches et D'Applications Scientifiques (S.C.R.A.S.) (FR)

( * ) Notice: Subject to any disclaimer, the term of this patent is extended or adjusted under 35 U.S.C. 154(b) by 82 days.

(21) Appl. No.: 10/111,139

(22) PCT Filed: Nov. 3, 2000

(86) PCT No.: PCT/FR00/03066

§ 371 (c)(1),
(2), (4) Date: Apr. 19, 2002

(87) PCT Pub. No.: WO01/32216

PCT Pub. Date: May 10, 2001

(30) Foreign Application Priority Data

Nov. 5, 1999 (FR) ............................................. 99 13859

(51) Int. Cl.$^7$ .............................................. A61K 45/06
(52) U.S. Cl. ...................................................... 514/365
(58) Field of Search ......................................... 514/365

(56) References Cited

U.S. PATENT DOCUMENTS 6,335,445 B1 * 1/2002 Chabrier de Lassauniere et al. .......................... 544/358

OTHER PUBLICATIONS

Holscher et al, "Inhibitors of . . . Spatial Task", Neuroreport (1995) vol. 6, No. 5, pp. 730–732, XP000923049.
Nishibori et al, "Effect of . . . Parotid Gland", Adv. Biosci. (1982), 33(Adv. Histamine Res.), pp. 203–209, XP000923046.

* cited by examiner

*Primary Examiner*—Fiona T. Powers
(74) *Attorney, Agent, or Firm*—Muserlian, Lucas and Mercanti

(57) ABSTRACT

The invention concerns a product comprising at least a NO synthase inhibiting substance associated with at least a phospholipase A2 inhibiting substance, separately or combined, for simultaneous therapeutic use, separately or spread over time for treating pathologies in which nitrogen monoxide and/or phospholipases A2 are involved. The invention also concerns a pharmaceutical composition comprising, an active principle, at least a NO synthase inhibiting substance and at least a phospholipase A2 inhibiting substance, and optionally a pharmaceutically acceptable.

11 Claims, No Drawings

PRODUCT COMPRISING AT LEAST A NO SYNTHASE INHIBITING SUBSTANCE ASSOCIATED WITH AT LEAST A PHOSPHOLIPASE A2 INHIBITING SUBSTANCE

This application is a 371 of PCT/FR00/03066 filed Nov. 3, 2000.

The invention relates to a product comprising at least one NO synthase inhibiting substance in association with at least one phospholipase A2 inhibiting substance, in separate form or in combination, for therapeutic use which is simultaneous, separate or spread over time in the treatment of pathologies in which nitrogen monoxide and/or the phospholipases A2 are involved. The invention also relates to a pharmaceutical composition comprising, as active ingredient, at least one NO synthase inhibiting substance and at least one phospholipase A2 inhibiting substance, and optionally a pharmaceutically acceptable support.

A product and a pharmaceutical composition according to the invention are useful in the treatment of pathologies in which nitrogen monoxide and the phospholipases A2 are involved, and in particular:

proliferative, inflammatory and edematous diseases such as, for example, atherosclerosis, recurrence of stenosis, pulmonary hypertension, glomerulonephritis, portal hypertension, psoriasis, arthrosis and rheumatoid arthritis, fibroses, amyloidoses, inflammations of the gastrointestinal system (colitis, Crohn's disease, pancreatitis) or of the pulmonary system and airways (asthma, sinusitis, respiratory distress syndrome), allergic rhinitis;

cardiovascular and cerebrovascular disorders comprising, for example, migraine, arterial hypertension, septic shock, cardiac or cerebral infarctions of ischemic or hemorrhagic origin, ischemia and thromboses;

disorders of the central or peripheral nervous system such as, for example, neurodegenerative diseases where there can in particular be mentioned cerebral infarctions, senile dementia, including Alzheimer's disease, Huntington's chorea, Parkinson's disease, Creutzfeld Jacob disease, diseases due to prions, amyotrophic lateral sclerosis and also pain, cerebral trauma or trauma of the spinal cord, addiction to opiates, to alcohol and to substances engendering addiction;

dermatitis, solar radiation (UVA, UVB);

organ transplants;

autoimmune and viral diseases such as for example lupus, AIDS, parasitic and viral infections, diabetes, multiple sclerosis, myopathies;

cancer and ophthalmic diseases;

and more generally all pathologies characterized by production or hyperactivation of nitrogen monoxide and/or phospholipase A2.

In all these pathologies, there is experimental evidence demonstrating the involvement of nitrogen monoxide (*J. Med. Chem.* (1995) 38, 4343–4362; *Clin. Exp. Immunol.* (1998) 113, 147–156) and the phospholipases A2 (*Trends Pharmac. Sci.* (1999), 20, 162–16170; *Brain Res. Bull.* (1999), 49, 139–153). This is the case in particular in experimental inflammation of the rat's paw which illustrates the invention (*Agents Actions* (1989) 26, 292–300; *Immunopharmacology* (1993), 26, 1–9; *Br. J. Pharmacol.* (1998), 123, 1119–1126).

In this context, the medicaments which can inhibit the formation of nitrogen monoxide or inhibit the phospholipases A2 can have beneficial effects. No association of these two active ingredients, namely an inhibitor of NO synthase and an inhibitor of the phospholipases A2, has been carried out. As is disclosed in the experimental part, the association of an inhibitor of NO synthases and an inhibitor of phospholipases A2, active ingredients which act by different mechanisms, causes an unexpected therapeutic effect of these active ingredients, namely that they act synergistically. In fact, when they are administered at subactive doses (i.e. at doses which do not in themselves have a therapeutic effect), they produce, in combination, a highly significant therapeutic effect.

The advantage of this association is that it significantly reduces the doses of each of the active ingredients and thus significantly reduces their undesirable effects while gaining in therapeutic effectiveness. This invention is particularly well illustrated in an experimental pathological model of inflammation of the rat's paw by carrageenan.

Firstly, a subject of the invention is a product comprising at least one NO synthase inhibiting substance in association with at least one phospholipase A2 inhibiting substance, in separate form or in combination, for therapeutic use which is simultaneous, separate or spread over time in the treatment of pathologies in which nitrogen monoxide and/or phospholipases A2 are involved. Preferably, said product will comprise an NO synthase inhibiting substance in association with an phospholipase A2 inhibiting substance.

By inhibitor of NO synthases, there should be understood any specific or non specific inhibitor of one of its isoforms whether constitutive (neuronal or endothelial) or inducible (*J. Med. Chem.* (1995) 38, 4343–4362). Preferably, the NO synthase inhibitors used for the present invention are inhibitors of the neuronal or inducible forms of NO synthases.

By inhibitor of phospholipases A2, there should be understood any specific or non specific inhibitor of one of the secreted or cellular forms of phospholipases A2 (*Medicine/Sciences* (1995) 12, 323–332; *Trends Pharmac. Sci.* (1999) 20, 16162–16170; *Brain Res. Bull.* (1999) 49, 139–153).

In a product according to the invention, the NO synthase inhibitor and the phospholipase A2 inhibitor can be presented in separate form or in combined form by forming a salt. Preferably, the salt is formed from a derivative of the NO synthase inhibiting substance containing at least one basic group and a derivative which inhibits phospholipases A2 containing at least one acid group. Thus salts can be formed, according to methods known to a person skilled in the art, from inhibitors of NO synthase such as for example amidines, guanidines, pyridines or piperidines as defined hereafter, and inhibitors of phospholipases A2 such as for example mepacrine, aristolochic acid, acylpyrroldicarboxylic or acylindoldicarboxylic acids as defined hereafter. These substances can be natural or synthetic.

A subject of the invention is also a product comprising at least one NO synthase inhibiting substance in association with at least one derivative which inhibits phospholipases A2, in separate form or in combination, for therapeutic use which is simultaneous, separate or spread over time in the treatment of pathologies in which nitrogen monoxide and/or phospholipases A2 are involved, such as in particular cardiovascular and cerebrovascular disorders, disorders of the central or peripheral nervous system, proliferative and inflammatory diseases, organ transplants, autoimmune and viral diseases, cancer, and more generally all pathologies characterized either by an excessive production of nitrogen monoxide and/or phospholipases A2, or by a dysfunction linked to nitrogen monoxide and/or phospholipases A2.

Among the inhibitors of NO synthases, there can be defined compounds of amino acid and non amino acid type.

The inhibitors of NO synthases of amino acid type can be compounds as described in Applications WO 95/00505, WO 94/12163, WO 96/06076 and Application EP 230037, incorporated by way of reference into the present Application, or derivatives of L-arginine, ornithine or lysine as described in PCT WO 95/22968, incorporated by way of reference into the present Application.

The non amino acid type inhibitors of NO synthases can be compounds of the guanidine, isothiourea, nitro- or cyano-aryl, amino-pyridine or amino-pyrimidine, amidine, indazole or imidazole families.

The guanidine derivatives which inhibit NO synthases can be compounds as defined in PCT Applications WO 95/28377, WO 91/04023, WO 94/21621, WO 96/18607 and WO 96/18608 incorporated by way of reference into the present Application.

The isothioureas which inhibit NO synthases can be compounds as defined in PCT Applications WO 95/09619, WO 96/09286, WO 94/12165, WO 96/14842, WO 96/18607, WO 96/18608, WO 96/09286 and Applications EP 717040 and EP 718294, incorporated by way of reference into the present Application.

The nitro- or cyano-aryl inhibitors of NO synthases can be compounds as defined in PCT Application WO 94/12163, incorporated by way of reference into the present Application.

The amino-pyridines or amino-pyrimidines which inhibit NO synthases can be compounds as defined in PCT Applications WO 94/14780, WO 96/18616 and WO 96/18617, incorporated by way of reference into the present Application.

The amidines which inhibit NO synthase can be compounds as defined in PCT Applications WO 95/11014, WO 96/01817, WO 95/05363, WO 95/11231, WO 96/14844 and WO 96/19440, incorporated by way of reference into the present Application, or compounds such as N-phenyl-2-thiophenecarboximidamide.

Moreover, the NO synthase inhibitors can also be both inhibitors of NO synthases (NOS) and reactive oxygen species (ROS) traps. The Applicant was the first to describe such inhibitors in PCT Patent Applications WO 98/42696, WO 98/58934, WO 00/02860, WO 00/17190 and WO 00/17191, incorporated by way of reference into the present Application (other unpublished patent applications describing compounds having such pharmacological activities have also been filed by the Applicant and the compounds described therein can also be used according to the present invention). These compounds also have a synergy in the experimental pathological model of inflammation of the rat's paw by carrageenan, whilst retaining the advantages already disclosed in PCT Applications WO 98/42696 and WO 98/58934, WO 00/02860, WO 00/17190 and WO 00/17191.

The indazoles which inhibit NO synthases can be compounds of general formula $I_A$

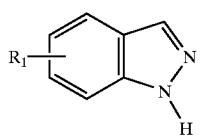

$I_A$ in which $R_1$ represents one or more substituents chosen from the hydrogen atom and the nitro, halo, alkyl or alkoxy radicals;

or pharmaceutically acceptable salts of the compounds of general formula $I_A$.

The imidazoles which inhibit NO synthases can be compounds of general formula $II_A$

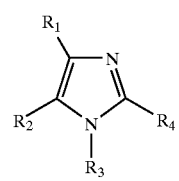

$II_A$ in which $R_1$ and $R_2$ represent, independently, a hydrogen atom or the halo, hydroxy, amino, alkyl or alkoxy radical, or $R_1$ and $R_2$ are linked together and form a phenyl radical condensed with the imidazole ring, said phenyl radical being optionally substituted by one or more substituents chosen from the hydroxy, trifluoromethyl, halo, carboxy, alkyl, alkoxy or alkenyl radicals;

$R_3$ represents a hydrogen atom or an alkyl, amino, alkylamino or phenyl radical, said phenyl radical being optionally substituted by one or more substituents chosen from the hydroxy, trifluoromethyl, halo, carboxy, alkyl, alkoxy or alkenyl radicals;

and $R_4$ represents a hydrogen atom or an alkyl, amino or alkylamino radical;

or pharmaceutically acceptable salts of the compounds of general formula $II_A$.

The NO synthase and ROS inhibiting compounds can in particular be the compounds of general formula $III_A$

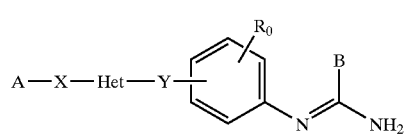

$III_A$ in which $R_0$ represents H or an alkyl radical;

A is a

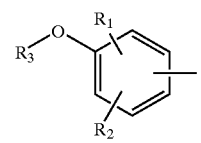

radical in which $R_1$ and $R_2$ represent, independently, a hydrogen atom, a halogen, the OH group, a linear or branched alkyl radical having 1 to 6 carbon atoms, a linear or branched alkoxy radical having 1 to 6 carbon atoms, and $R_3$ represents a hydrogen atom, a linear or branched alkyl radical having 1 to 6 carbon atoms or a —$COR_4$ radical, $R_4$ representing an alkyl radical having 1 to 6 carbon atoms, or a

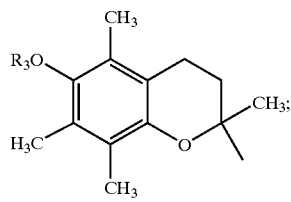

radical in which R₃ represents a hydrogen atom, a linear or branched alkyl radical having 1 to 6 carbon atoms or a —COR₄ radical, R₄ representing an alkyl radical having 1 to 6 carbon atoms;

B represents a linear or branched alkyl radical having 1 to 6 carbon atoms, phenyl, pyridinyl or a heterocycle with 5 members containing 1 to 4 heteroatoms chosen from O, S, N and more particularly: thiophene, furane, pyrrole or thiazole, the carbons of which are optionally substituted by one or more groups chosen from an alkyl radical having 1 to 6 linear or branched carbon atoms, an alkoxy radical having 1 to 6 carbon atoms or a halogen;

X represents —CO—N(R₃)—X'—, —NH—CO—X'—, —CH=, —CO— or a bond, with X' representing —(CH₂)ₙ-, n being an integer from 0 to 6;

Y represents —Y'—, —CO—NH—Y'—, —Y'—NH—CO—, —CO—Y'—, —Y'—CO, —N(R₃)—Y'—, —Y'—N(R₃)—, Y'—CH₂—N(R₃)—CO—, —O—Y'—, —Y'—O—, —S—Y'—, —Y'—S—, —Y'—O—Y'—, —Y'—N(R₃)—Y'— or a bond, with Y'representing —(CH₂)ₙ—, n being an integer from 0 to 6;

Het represents a heterocycle comprising 1 to 5 heteroatoms chosen from O, N, S being able to be substituted by one or more substituents X'—OR₃, X'—NR₃, X'—S—R₃ and such as for example:

oxetane, pyrrole, pyrrolidine, furane, tetrahydrofuran, thiophene, tetrahydrothiophene, sulpholane, piperazine, homopiperazine, 4-aminopiperidineimidazole, imidazoline, dihydroimidazole-2-one, dihydroimidazole-2-thione, oxazole, isoxazole, oxazoline, isoxazoline, oxazolidine, oxazolidinone, thiazole, thiazoline, thiazolidine, thiazolidinone, hydantoin, 1,2,4-triazole, 1,3,4-oxadiazole, 1,3,4-thiadiazole, 1,1-dioxide-1,2,5-thiadiazolidine, 1,2,4-triazole-3-one, tetrazole, tetrahydropyridine, azetidine;

or pharmaceutically acceptable salts of the latter.

In certain cases, the compounds of the present invention can comprise asymmetrical carbon atoms. As a result, the compounds of the present invention have two possible enantiomeric forms, i.e. the "R" and "S" configurations. The compounds of the present invention include the two enantiomeric forms and all combinations of these forms, including the "RS" racemic mixtures. In an effort to simplify matters, when no specific configuration is indicated in the structural formulae, it should be understood that both enantiomeric forms and their mixtures are represented.

By alkyl, unless specified otherwise, is meant a linear or branched alkyl radical containing 1 to 6 carbon atoms. By alkenyl, unless specified otherwise, is meant a linear or branched alkyl radical containing 1 to 6 carbon atoms and having at least one unsaturation (double bond). By haloalkyl is meant an alkyl radical at least one of the hydrogen atoms of which (and optionally all) is replaced by a halogen atom.

By alkoxy, alkenyl or alkylamino radicals, are meant respectively the alkoxy, alkenyl or alkylamino radicals the alkyl radical of which has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. Finally, by halogen is meant the fluorine, chlorine, bromine or iodine atoms.

By pharmaceutically acceptable salt is meant in particular the addition salts with inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. When they can be used, the salts formed from bases such as sodium or potassium hydroxide also fall within the scope of the present invention. For other examples of pharmaceutically acceptable salts, reference can be made to "Salt selection for basic drugs", *Int. J. Pharm.* (1986), 33, 201–217.

Among the phospholipase A2 inhibitors, there can be defined the compounds of the following types: acylpyrroldicarboxylic acids, acylindoldicarboxylic acids and pyrrolidine derivatives. The phospholipase A2 inhibitors of acylpyrroldicarboxylic acid, acylindoldicarboxylic acid and pyrrolidine derivative type can be compounds as described in Applications EP 97934481, WO 98/05637, EP 969225076 and WO 98/33797. The phospholipase A2 inhibitors can also be compounds as defined in Applications WO 99/43672, WO 99/43654, WO 99/43651, WO 99/15493 and WO 98/37069. The phospholipase A2 inhibitors can in particular also be arylsulphonamide derivatives as described in Application WO 98/25893, 1H-indole-3-glyoxylamide derivatives as described in Application WO 99/57100, indole derivatives as described in Application WO 00/07591 or 2-phenylpyrimidine derivatives as described in Application WO 00/27824. All the aforementioned patent applications are incorporated into the present Application by way of reference.

According to the invention, the inhibitors of phospholipases A2 are preferably:

the compounds of general formula $I_B$ or $I'_B$

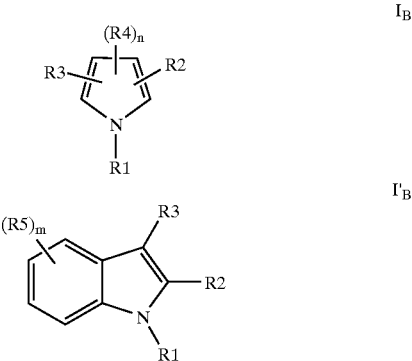

in which

R1 represents a —Y1-Ar—Y2-Y3 group in which Y1 and Y2 represent independently a $(C_1-C_{12})$-alkyl, $(C_2-C_{12})$-alkenyl, $(C_1-C_{12})$-alkoxy or $(C_1-C_{12})$alkenyloxy radical, the Y1 and Y2 radicals where appropriate being able to be interrupted by one or more oxygen atoms, Ar is an aryl group optionally substituted 1 to 3 times by substituents chosen independently from the R6, R7 and R8 groups, and Y3 represents a —COOR17, —CONR17R17, —CONHCOR19, —CONHS(O)₂R19, —CONHNHS(O)₂R19 or Tz radical;

R2 represents —COOR17, —Y4-COOR17, —CONR17R17, —Y4-CONR17R17, —CONHCOR19, —Y4-CONHCOR19, —CONHS(O)₂R19, —Y4-

CONHS(O)$_2$R19, —CONHNHS(O)$_2$R19, —Y4-CONHNHS(O)$_2$R19, Tz or —Y4-Tz, with Y4 representing a (C$_1$–C$_8$)-alkyl, (C$_2$–C$_8$)-alkenyl radical, the Y4 radical where appropriate being able to be interrupted by one or more oxygen atoms;

R3 represents a —CO—R9 radical in which R9 represents a —Y5, aryl or —Y5-aryl radical, with Y5 representing a (C$_1$–C$_9$)-alkyl, (C$_2$–C$_{19}$)-alkenyl or (C$_2$–C$_{19}$)-alkynyl radical, the Y5 radical where appropriate being able to be interrupted by one or more oxygen atoms and the aryl radical of R9 being optionally substituted 1 to 3 times by substituents chosen independently from the R10, R11 and R12 groups;

each R4 radical independently represents a hydrogen atom, a halogen atom, —CF$_3$, —Y6, aryl or —Y6-aryl, with Y6 representing a (C$_1$–C$_8$)-alkyl, (C$_2$–C$_8$)-alkenyl or (C$_2$–C$_8$)-alkynyl radical, the Y5 radical where appropriate being able to be interrupted by one or more oxygen atoms and the aryl radical of R4 being optionally substituted 1 to 3 times by substituents chosen independently from the R13, R14 and R15 groups and two neighbouring Y6 alkyl radicals being able to form together with the carbon atoms to which they are attached a ring with 5 to 8 members which can itself where appropriate be substituted by one or two (C$_1$–C$_4$)-alkyl radicals;

n represents the FIG. 2 and m represents the FIG. 4;

Tz is a 1H- or 2H-tetrazol-5-yl radical;

the R6, R7, R8, R10, R11, R12, R13, R14, R15 and R16 radicals are chosen independently from the group comprising the (C$_1$–C$_{20}$)-alkyl, (C$_2$–C$_{20}$)-alkenyl or (C$_2$–C$_{20}$)-alkynyl radicals optionally interrupted by one or more oxygen atoms, a halogen atom, the —CF$_3$, —CN, —NO$_2$ or —COCH$_2$OH groups and a perhalo (C$_1$–C$_6$)-alkenyl, —OR17, —SR17, —COOR17, —COR18, —NHCOR17, —NR17R17, —NHS(O)$_2$R17, —SOR17, —S(O)$_2$R17, —CONR17R17, —S(O)$_2$NR17R17, —OOCR18, —OOCNR17R17, —OOCOR17, —(CH$_2$)$_r$OR23, —(CH$_2$)$_r$SR23, CH$_2$)$_r$NHR23 or —(CH$_2$)$_s$R20 radical;

R17 represents, independently each time it occurs, a —(CH$_2$)$_r$R20 radical or one of the (C$_1$–C$_{20}$)-alkyl, (C$_2$–C$_{20}$)alkenyl or (C$_2$–C$_{20}$)-alkynyl radicals optionally interrupted by one or more oxygen atoms;

R18 represents, independently each time it occurs, an R17, —CF$_3$, —(CH$_2$)$_u$COOH or —(CH$_2$)$_u$COOR21 radical;

R19 represents, independently each time it occurs, an R17 or —CF$_3$ radical;

R20 represents, independently each time it occurs, an aryl radical substituted by one or two R22 groups;

R21 represents, independently each time it occurs, a (C$_1$–C$_6$)-alkyl, benzyl or phenyl radical;

R22 represents, independently each time it occurs, a hydrogen atom, a halogen atom, a (C$_1$–C$_{12}$)-alkyl, (C$_1$–C$_{12}$)-alkoxy, (C$_1$–C$_{12}$)-alkylthio, (C$_1$–C$_{12}$)-alkylsulphonyl, (C$_1$–C$_{12}$)-alkylcarbonyl, —CF$_3$, —CN or —NO$_2$ radical;

R23 represents, independently each time it occurs, a hydrogen atom or a —COR21 radical;

r is an integer from 1 to 20;

s and t independently represent integers from 0 to 12;

and u represents an integer from 0 to 4;

or the compounds of general formula II$_B$

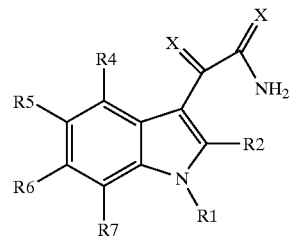

in which
the two X groups represent oxygen atoms;
R1 is chosen from the group constituted by the

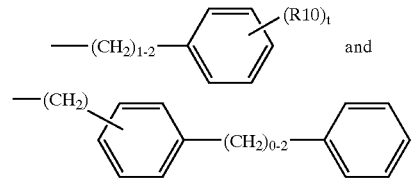

radicals, in which R10 is chosen independently from a halogen atom and a (C$_1$–C$_{10}$)-alkyl, (C$_1$–C$_{10}$)-alkoxy, (C$_1$–C$_{10}$)-alkylthio and (C$_1$–C$_{10}$)-haloalkyl radical and t is an integer from 0 to 5;

R2 is chosen from a halogen atom and a cyclopropyl, methyl, ethyl or propyl radical;

R4 and R5 are chosen independently from a hydrogen atom, a substituent which does not interfere or the (acid)-L$_a$-(acid group) group, it being understood that —L$_a$— for R4 is chosen from —O—CH$_2$—, —S—CH$_2$—, —NH—CH$_2$—, —CH$_2$—CH$_2$—, —O—CH(CH$_3$)— and —O—CH(CH$_2$—CH$_2$—Ph)—, Ph being a phenyl radical and that —L$_a$— for R5 is chosen from the

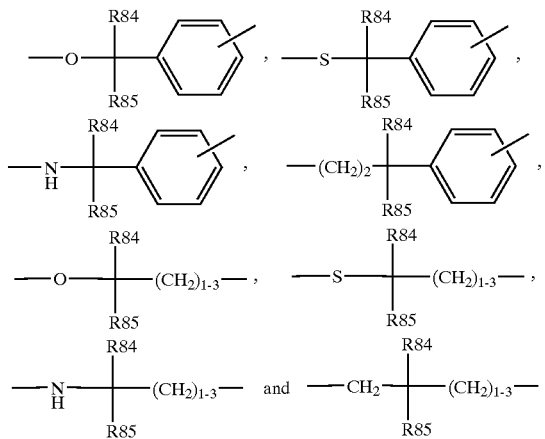

radicals in which R84 and R85 are chosen independently from a hydrogen atom, a halogen atom and a (C$_1$–C$_{10}$)-alkyl, aryl, (C$_1$–C$_{10}$)-alkaryl, (C$_1$–C$_{10}$)-aralkyl, carboxy or carbalkoxy radical, it being understood also that at least one of R4 and R5 must be the —L$_a$-(acid group) group and that the (acid group) of R4 and R5 is chosen from —CO$_2$H, —SO$_3$H and —P(O)(OH)$_2$;

R6 and R7 are chosen independently from a hydrogen atom and a substituent which does not interfere;

the substituents which do not interfere being chosen independently from the group comprising the following radicals:

($C_1$–$C_6$)-alkyl, ($C_2$–$C_6$)-alkenyl, ($C_2$–$C_6$)alkynyl, ($C_7$–$C_{18}$)-aralkyl, ($C_7$-$C)_8$)-alkaryl, ($C_3$-$C_8$)-Cycloalkyl, ($C_3$-Cg)-cycloalkenyl, phenyl, toluyl, xylenyl, phenylmethyl, ($C_1$–$C_6$)-alkoxy, ($C_2$–$C_6$)-alkenyloxy, ($C_2$–$C_6$)-alkynyloxy, ($C_2$–$C_{12}$)-alkoxyalkyl, ($C_2$–$C_{12}$)-alkoxyalkyloxy, ($C_2$–$C_{12}$)-alkylcarbonylamino, ($C_2$–$C_{12}$)-alkoxyamino, ($C_2$–$C_{12}$)-alkoxyaminocarbonyl, ($C_2$–$C_{12}$)-alkylamino, ($C_1$–$C_6$)-alkylthio, ($C_2$–$C_{12}$)-alkylthiocarbonyl, ($C_1$–$C_6$)-alkylsulphinyl, ($C_1$–$C_6$)-alkylsulphonyl, ($C_2$–$C_6$)-haloalkoxy, ($C_2$–$C_6$)-haloalkylsulphonyl, ($C_2$–$C_6$)-haloalkyl, ($C_1$–$C_6$)-hydroxyalkyl, —C(O)O((($C_1$–$C_6$)-alkyl), —(CH$_2$), —O—(($C_1$–$C_6$)-alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl and ($C_1$–$C_6$)-alkylcarbonyl, n being an integer from 1 to 8;

or the compounds of general formula III$_B$

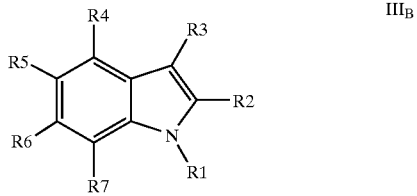

III$_B$ in which
R1 is chosen from the groups (a), (b) and (c);
(a) represents a ($C_7$–$C_{20}$)-alkyl, ($C_7$–$C_{20}$)-haloalkyl, ($C_7$–$C_{20}$)alkenyl or ($C_7$–$C_{20}$)-alkynyl radical, a saturated or unsaturated carbon ring with 5 to 14 members optionally substituted by one or more substituents chosen from substituents which do not interfere, or also (a) represents a heterocycle with 5 to 14 members containing 1 to 3 heteroatoms, said heterocycle being saturated or unsaturated and optionally substituted by one or more substituents chosen from substituents which do not interfere;
(b) is one of the (a) radicals substituted by one or more substituents chosen from substituents which do not interfere;
(c) represents the —(L$_1$)—R11 group in which —(L$_1$)— is a group chosen from the groups represented by the formulae

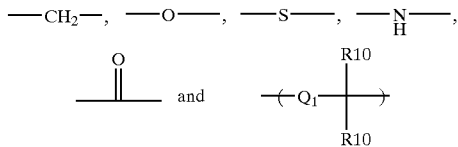

in which Q$_1$ represents a bond or one of the —CH$_2$—, —O—, —S—, —NH— and —CO— groups and each of the R10 groups independently represents a hydrogen atom or a ($C_1$–$C_8$)-alkyl, ($C_1$–$C_8$)-haloalkyl or ($C_1$–$C_8$)-alkoxy radical,
and R11 is a group chosen from the groups (a) and (b);
R2 is a hydrogen atom, a halogen atom, or a ($C_1$–$C_4$)-alkyl, ($C_2$–$C_4$)-alkenyl, —O—($C_1$–$C_3$)-alkyl, —S—($C_1$–$C_3$)-alkyl, —($C_1$–$C_4$)-cycloalkyl, —CF$_3$, —NO$_2$, —CN or —SO$_3$ radical;
R3 represents —(L$_3$)—Z in which —(L$_3$)— is a divalent bond group chosen from a bond and the —CH$_2$—, —O—, —S—, —NH— and —CO— groups;

and Z is chosen from the acetamide, thioacetamide, glyoxylamide, thioglioxylamide, hydrazide or thiohydrazide groups represented by the general formulae

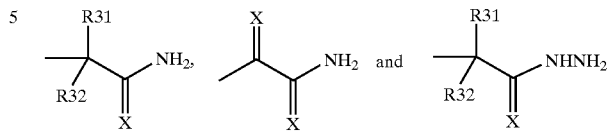

in which R31 and R32 are chosen independently from a hydrogen atom and a ($C_1$–$C_8$)-alkyl, ($C_1$–$C_8$)-haloalkyl or ($C_3$–$C_4$)-cycloalkyl radical and X represents, independently each time it occurs, an oxygen or sulphur atom;
R4 and R5 are chosen independently from a hydrogen atom, a substituent which does not interfere or the —(L$_a$)-(acylsulphonamide group) group in which —(L$_a$)— for R4 is a group represented by the formula

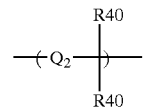

in which Q$_2$ is chosen from —CH$_2$—, —O—, —NH—, —C(O)— and —S—, and each of the R40 groups is chosen independently from a hydrogen atom, a halogen atom and the ($C_1$–$C_8$)-alkyl, aryl, ($C_1$–$C_8$)-alkaryl, ($C_1$–$C_8$)-alkoxy and aralkyl radicals,
—(L$_a$)— for R5 is chosen from the groups represented by the formulae

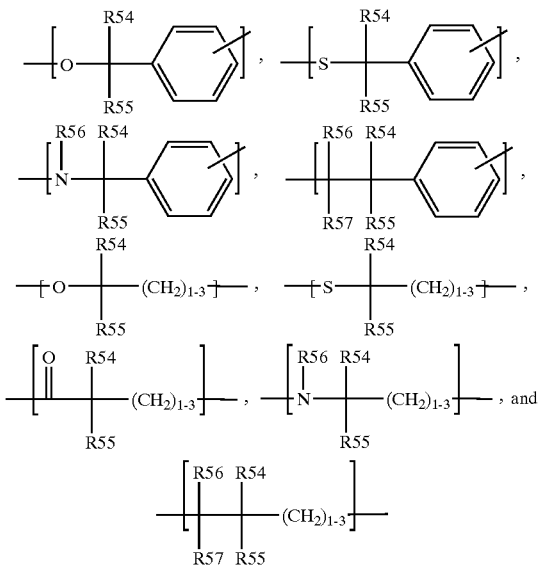

in which R54, R55, R56 and R57 are independently chosen from the group comprising a hydrogen atom, a halogen atom and the ($C_1$–$C_8$)-alkyl, ($C_1$–$C_8$)-alkoxy, ($C_1$–$C_8$)-haloalkyl and aryl radicals,
the (acylsulphonamide) group being a group of formula —CO—NH—SO$_2$—R81 in which R81 is chosen from the group comprising the —CF$_3$, ($C_1$–$C_8$)-alkyl, ($C_1$–$C_8$)-alkoxy, ($C_1$–$C_8$)-alkylthio, ($C_1$–$C_8$)-alkylamino, ($C_1$$C_8$)-haloalkyl, ($C_1$–$C_{14}$)-aralkyl, ($C_1$–$C_{14}$)-alkylaryl, aryl, thioaryl, ($C_3$–$C_{14}$)-cycloalkyl radicals and a heterocycle with 3 to 14 members, said heterocycle containing 1 to 3 heteroatoms and being saturated or unsaturated, it being understood moreover that at least one of R4 and R5 is an —(L_a)-(acylsulphonamide group) group;

R6 and R7 represent independently a hydrogen atom, a substituent which does not interfere, a carbon ring with 5 to 14 saturated or unsaturated members optionally substituted by one or more substituents chosen from substituents which do not interfere or a heterocycle with 5 to 14 members containing 1 to 3 heteroatoms, said heterocycle being saturated or unsaturated and optionally substituted by one or more substituents chosen from substituents which do not interfere;

substituents which do not interfere being chosen independently from the group comprising the following radicals: ($C_1$–$C_8$)-alkyl, ($C_2$–$C_8$)-alkenyl, ($C_2$–$C_8$)-alkynyl, ($C_7$–$C_{12}$)-aralkyl, ($C_7$–$C_{12}$)-alkaryl, ($C_3$–$C_8$)-cycloalkyl, ($C_3$–$C_8$)-cycloalkenyl, phenyl, toluyl, xylenyl, biphenyl, ($C_1$–$C_8$)-alkoxy, ($C_2$–$C_8$)-alkenyloxy, ($C_2$–$C_8$)-alkynyloxy, ($C_2$–$C_{12}$)-alkoxyalkyl, ($C_2$–$C_{12}$)-alkoxyalkyloxy, ($C_2$–$C_{12}$)-alkylcarbonyl, ($C_2$–$C_{12}$)-alkylcarbonylamino, ($C_2$–$C_{12}$)-alkoxyamino, ($C_2$–$C_{12}$)-alkoxyaminocarbonyl, ($C_1$–$C_{12}$)-alkylamino, ($C_1$–$C_6$)-alkylthio, ($C_2$–$C_{12}$)-alkylthiocarbonyl, ($C_1$–$C_8$)-alkylsulphinyl, ($C_1$–$C_8$)-alkylsulphonyl, ($C_2$–$C_8$)-haloalkoxy, ($C_1$–$C_8$)-haloalkylsulphonyl, ($C_2$–$C_8$)-haloalkyl, ($C_1$–$C_8$)-hydroxyalkyl, —C(O)O(($C_1$–$C_8$)-alkyl), —($CH_2$)$_n$—O($C_1$–$C_8$)-alkyl), benzyloxy, phenoxy, phenylthio, —CONHSO$_2$R, —CHO, amino, amidino, bromo, carbamyl, carboxyl, carbalkoxy, —($CH_2$)$_n$—$CO_2$H, chloro, cyano, cyanoguanidinyl, fluoro, guanidino, hydrazide, hydrazino, hydrazido, hydroxy, hydroxyamino, iodo, nitro, phosphono, —$SO_3$H, thioacetal, thiocarbonyl, n being an integer from 1 to 8 and R being a ($C_1$–$C_8$)-alkyl radical;

or the compounds of general formula IV$_B$

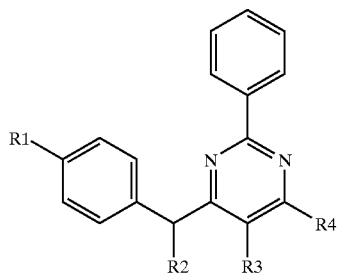

in which

R1 is chosen from the group comprising a halogen atom and the ($C_1$–$C_6$)-alkyl or ($C_1$–$C_6$)-alkoxy radicals;

R2 is chosen from the group comprising one of the phenyl or benzyl radicals optionally substituted on the aromatic ring by a halogen atom or a ($C_1$–$C_6$)-alkyl, ($C_1$–$C_6$)-alkoxy, amino, alkylamino, dialkylamino, carboxyl, carbamoyl, ($C_1$–$C_6$)-acyl, sulphonyl, thiol or alkylthio radical, and a ($C_3$–$C_7$)-cycloalkyl radical, said ($C_3$–$C_7$)-cycloalkyl radical being optionally condensed with a benzene ring or a heterocycle and being optionally substituted by a halogen atom or a ($C_1$–$C_6$)-alkyl radical;

R3 is chosen from the group comprising a halogen atom and a ($C_1$–$C_6$)-alkyl radical;

and R4 is chosen from the group comprising —H, —OH, —$N_3$ and —NHCOCH$_3$;

or also the pharmaceutically acceptable salts of the compounds of general formula I$_B$, II$_B$, III$_B$ or IV$_B$.

According to another preferred variant, the phospholipase A2 inhibitors can be chosen from the group constituted by mepacrine, aristolochic acid and their analogues, as well as the pharmaceutically acceptable salts of the latter.

A more particular subject of the invention is a product as defined above, characterized in that:

the NO synthase inhibitor(s) are chosen from the group constituted by L-nitro-arginine (LNA), L-nitro-arginine methyl ester (LNAME), L-N-monomethylarginine (LNMMA), aminoguanidine, agmatine, 2-amino-1-(methylamino)benzimidazole, 5-nitro-indazole, 6-nitro-indazole, 7-nitro-indazole, 1,2-(trifluoromethylphenyl)imidazole (TRIM), 2-amino-4-methyl-6-(2-aminoethyl)pyridine, 2-iminopiperidine, 2-iminohomopiperidine, 2-imino-5,6-dihydro-1,3-thiazine, 2-imino-5,6-dihydro-1,3-oxazine, N-phenyl-2-thiophenecarboximidamide, 2-iminotetrahydropyrimidine, S-ethylisothiourea, S-methyl-L-thiocitrulline, S-ethyl-L-thiocitrulline, (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide and 4-[3,5-bis(1,1-dimethylethyl)-4-hydroxyphenyl]-N-{4-[(imino(2-thienyl)methyl)amino]phenyl}-N-methyl-2-thiazolemethanamine, as well as the pharmaceutically acceptable salts of the latter; and the phospholipase A2 inhibitor(s) are chosen from the group constituted by mepacrine and aristolochic acid and their analogues, as well as the pharmaceutically acceptable salts of the latter.

Even more preferentially, a subject of the invention is a product as defined above, characterized in that:

the NO synthase inhibitor(s) are chosen from the group constituted by aminoguanidine, 7-nitro-indazole and 4-[3,5-bis(1,1-dimethylethyl)-4-hydroxyphenyl]-N-{4-[(imino(2-thienyl)methyl)amino]phenyl}-N-methyl-2-thiazole-methanamine, as well as pharmaceutically acceptable salts of the aforementioned compounds; and the phospholipase A2 inhibitor(s) are chosen from the group constituted by mepacrine, aristolochic acid and their analogues, as well as pharmaceutically acceptable salts of the latter.

As already indicated, a product according to the invention can be used in the treatment of pathologies in which nitrogen monoxide and/or phospholipases A2 are involved. These pathologies include in particular cardiovascular and cerebrovascular disorders, disorders of the central or peripheral nervous system, proliferative and inflammatory diseases, diarrheas, vomiting, radioactive irradiation, solar radiation, organ transplants, autoimmune and viral diseases, cancer, and more generally all pathologies characterized either by an excessive production of nitrogen monoxide and/or phospholipases A2, or by a dysfunction linked with nitrogen monoxide and/or phospholipases A2.

According to a preferred variant, a product according to the invention can be used in the treatment of pathologies chosen from proliferative and inflammatory diseases such as atherosclerosis, pulmonary hypertension, glomerulonephritis, portal hypertension, psoriasis, arthrosis and rheumatoid arthritis, fibroses, amyloidoses and inflammations of the gastrointestinal system or of the pulmonary system and airways.

According to an also preferred variant, a product according to the invention can be used in the treatment of autoimmune and viral diseases such as lupus, AIDS, parasitic and viral infections, diabetes, multiple sclerosis or myopathies.

A subject of the invention is also a pharmaceutical composition comprising, as active ingredient, at least one NO synthase inhibiting substance and at least one phospholipase A2 inhibiting substance, and optionally a pharmaceutically acceptable support.

Preferably, said pharmaceutical composition will comprise, as active ingredient, an NO synthase inhibiting substance and an phospholipase A2 inhibiting substance.

Generally, the pharmaceutical compositions according to the invention will comprise a product as described previously, the same preferences remaining applicable.

In a pharmaceutical composition or product according to the invention, the inhibitor of NO synthases and the inhibitor of phospholipases A2 can be presented at doses which can be identical or different. The doses are chosen as a function of the compounds, associated with appropriate diluents or excipients.

The NO synthase inhibitor and the phospholipase A2 inhibitor can be administered simultaneously or sequentially, by the same administration route or by different routes, depending whether they are in separate or combined form. Preferably, the administration routes are oral, parenteral or topical.

A pharmaceutical composition according to the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

Pharmaceutical compositions containing a product according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The NO synthase inhibiting compounds and the phospholipase A2 inhibiting compounds are commercially available or can be prepared by the methods known to a person skilled in the art (or by analogy with the latter). In particular, the compounds of general formula $III_A$ are described in the PCT Applications WO 98/42696 and WO 98/58934 and the compounds of general formulae $I_B$ and $I'_B$, $II_B$, $III_B$ and $IV_B$ are described respectively in the PCT Patent Applications WO 98/05637, WO 99/57100, WO 00/07591 and WO 00/27824.

Unless they are defined differently, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

Experimental Part:

Pharmacological Study of the Products of the Invention

The activity of the compounds of the invention was evaluated in vivo on a model of carrageenan-induced rat's paw edema.

Male Sprague Dawley rats (Charles River) weighing 170 to 180 g on the day of the experiment are kept indoors for 5 to 8 days under animal husbandry conditions and are starved for 18 hours on a mesh floor before and during the experiment. The groups are constituted by 8 animals. The products are administered by intraperitoneal route (ip, 2 ml/kg), 30 minutes before the 1% Carrageenan is injected into the sole of the rats' rear right paw. The volume of the paw corresponding to the edema is measured using a water plethysmometer (Ugo Basile, APELEX) before the injection of carrageenan ($t_0$) and 3 hours after the injection. The volume of the paw allows determination of the % of inflammation ((volume of the paw at time t after carrageenan-volume of the same paw at time to before injection of the products/volume of the paw at time $t_0$)×100). Any product capable of significantly reducing the intensity of the edema (% of inflammation) is considered to be active. This effectiveness is determined statistically by a Student test.

In the following examples, A designates the NO synthase inhibitor and B designates the phospholipase A2 inhibitor.

EXAMPLE 1

Compound AB, a combination of active ingredients A and B. Compound A: 7-nitroindazole, an inhibitor of the neuronal form of NO synthases. Compound B: mepacrine, an phospholipase A2 inhibitor.

Compound of Example 1: 4 groups of animals are formed:

Group 1: treated with the vehicle+carrageenan.

Group 2: treated with A (25 mg/kg)+carrageenan.

Group 3: treated with B (30 mg/kg)+carrageenan.

Group 4: treated with AB+carrageenan.

| Group no. | % inflammation |
| --- | --- |
| 1 | 58.9 ± 4 |
| 2 | 72.5 ± 16.1 |
|   | IS |
| 3 | 64.5 ± 3.7 |
|   | IS |
| 4 | 28 ± 6.2 |
|   | *** |

(IS: insignificant result; ***: highly significant result)

The results demonstrate that 7-nitroindazole (an inhibitor of neuronal NO synthase) and mepacrine are inactive in protecting the animal from thc edema caused by carrageenan. On the other hand, the association of the two compounds protects the animals from the edema caused by carrageenan to a highly significant extent.

EXAMPLE 2

Compound AB, a combination of active ingredients A and B in separate form, where compound A is aminoguanidine, an inhibitor of the inducible form of NO synthases; and compound B is mepacrine, an inhibitor of phospholipases A2.

Compound of Example 2: 4 groups of animals are formed:

Group 1: treated with the vehicle+carrageenan.

Group 2: treated with A (400 mg/kg)+carrageenan.

Group 3: treated with B (30 mg/kg)+carrageenan.

Group 4: treated with AB+carrageenan.

| Group no. | % inflammation |
| --- | --- |
| 1 | 54.3 ± 2.5 |
| 2 | 53.1 ± 3.4 |
|   | IS |
| 3 | 53.9 ± 3.2 |
|   | IS |
| 4 | 33 ± 5 |
|   | ** |

(IS: insignificant result; **: highly significant result)

The results demonstrate that aminoguanidine (an inhibitor of inducible NO synthase) and mepacrine are inactive in protecting the animal from the edema caused by carrageenan. On the other hand, the association of the two compounds protects the animals from the edema caused by carrageenan to a highly significant extent.

EXAMPLE 3

Compound AB, a combination of active ingredients A and B in separate form, where compound A is aminoguanidine, an inhibitor of the inducible form of NO synthases; and compound B is aristolochic acid, an inhibitor of phospholipases A2.

Compound of Example 3: 4 groups of animals are formed:

Group 1: treated with the vehicle+carrageenan.
Group 2: treated with A (400 mg/kg)+carrageenan.
Group 3: treated with B (30 mg/kg)+carrageenan.
Group 4: treated with AB+carrageenan.

| Group no. | % inflammation |
|---|---|
| 1 | 57.1 ± 3.9 |
| 2 | 60.7 ± 7.5 IS |
| 3 | 68 ± 5.1 IS |
| 4 | 39.1 ± 4.5 ** |

(IS: insignificant result; **: highly significant result)

The results demonstrate that the aminoguanidine (an inhibitor of inducible NO synthase) and aristolochic acid are inactive in protecting the animal from the edema caused by carrageenan. On the other hand, the association of the two compounds protects the animals from the edema caused by the carrageenan to a highly significant extent.

EXAMPLE 4

Compound AB, a combination of the active ingredients A and B in separate form, where compound A is 4-[3,5-bis(1,1-dimethylethyl)-4-hydroxyphenyl]-N-{4-[(imino(2-thienyl)methyl)amino]phenyl}-N-methyl-2-thiazolemethanamine hydrochloride, a combined inhibitor of the neuronal form of NO synthases and of lipidic peroxidation; and compound B is mepacrine, an inhibitor of phospholipases A2.

Compound of Example 4: 4 groups of animals are formed:

Group 1: treated with the vehicle+carrageenan.
Group 2: treated with A (30 mg/kg)+carrageenan.
Group 3: treated with B (30 mg/kg)+carrageenan.
Group 4: treated with AB+carrageenan.

| Group no. | % inflammation |
|---|---|
| 1 | 51.5 ± 2.2 |
| 2 | 52.8 ± 4.0 IS |
| 3 | 51.9 ± 2.7 IS |
| 4 | 37.4 ± 4.6 * |

(IS: Insignificant result; *: significant result)

Here also, whereas 4-[3,5-bis(1,1-dimethylethyl)-4-hydroxyphenyl]-N-{4-[(imino(2-thienyl)methyl)amino]phenyl}-N-methyl-2-thiazole-methanamine hydrochloride (an inhibitor of neuronal NO synthase and an antioxidant) and mepacrine are inactive in protecting the animal from the edema caused by carrageenan, the association of the two compounds protect the animals from the edema caused by carrageenan to a significant extent.

The experimental results of Examples 1, 2, 3 and 4 therefore demonstrate a synergistic effect on the activity between the two types of compounds.

CONCLUSION

The results demonstrate that the administration of an NO synthase inhibitor and an phospholipase A2 inhibitor which are inactive alone, have a synergistic anti-inflammatory effect when associated.

What is claimed is:

1. A method of treating a disorder selected from the group consisting of cardiovascular and cerebrovascular disorders, disorders of the central or peripheral nervous system, proliferative and inflammatory diseases, diarrheas, vomiting, radioactive irradiation, solar radiation and organ transplants, in warm-blooded animals comprising administering to warm-blooded animals in need thereof an amount of a product comprising at least one NO synthase inhibiting substance of the formula

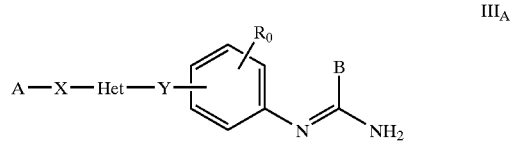

III$_A$ wherein R$_0$ is hydrogen or alkyl;
A is

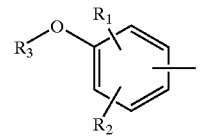

wherein R$_1$ and R$_2$ are individually selected from the group consisting of hydrogen, halogen, OH alkyl of 1 to 6 carbon atoms and alkoxy of 1 to 6 carbon atoms, and R$_3$ is selected from the group consisting of hydrogen, alkyl of 1 to 6 carbon atoms and —COR$_4$, R$_4$ is alkyl of 1 to 6 carbon atoms, or A is

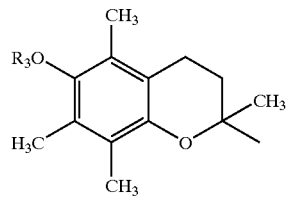

wherein R$_3$ is selected from the group consisting of hydrogen, alkyl of 1 to 6 carbon atoms and —COR$_4$, R$_4$ is alkyl of 1 to 6 carbon atoms;

B is selected from the group consisting of alkyl of 1 to 6 carbon atoms, phenyl, pyridinyl and a heterocycle with 5 members containing 1 to 4 heteroatoms selected from the group consisting of O, S and N, the carbons which are unsubstituted or substituted by at least one member of the group consisting of alkyl of 1 to 6 carbon atoms, alkoxy of 1 to 6 carbon atoms and halogen;

X is selected from the group consisting of —CO—N(R$_3$)—X'—, —NH—CO—X'—, —CH=, —CO— and a bond, X' is —(CH$_2$)$_n$, n is an integer from 0 to 6;

Y is selected from the group consisting of —Y'—, —CO—NH—Y', —Y'—NH—CO, —CO—Y'—, —Y'—CO, —N(R$_3$)—Y'—, —Y'—N(R$_3$)—, Y'—(CH$_2$—N(R$_3$)—CO—, —O—Y'—, —Y'—O—; —S—Y'—, —Y'—S—, —Y'—O—Y'—, —Y'—N(R$_3$)—Y'— and a bond, Y' is —(CH$_2$)$_n$— where n is an integer from 0 to 6;

Het is a heterocycle comprising 1 to 5 heteroatoms selected from the group consisting of O, N, S and unsubstituted or substituted by at least one member of the group consisting of —X'—OR$_3$, —X'—NR$_3$ and —X'S—R$_3$, and a pharmaceutically acceptable salt thereof in association with at least one phospholipase A2 inhibiting substance, in separate form or in combination, sufficient to treat said disorder.

2. The method of claim 1 wherein the NO synthase inhibiting substance is a substance inhibiting the neuronal form of NO synthases.

3. The method of claim 1 wherein the NO synthase inhibiting substance is a substance inhibiting the inducible form of NO synthases.

4. The method of claim 1 wherein the NO synthase inhibiting substance and phospholipase A2 inhibiting substance are administered separately.

5. The method of claim 1 wherein the NO synthase inhibiting substance and the phospholipase A2 inhibiting substance are in the form of salts.

6. The method of claim 5 wherein the salt is formed from a derivative of the NO synthase inhibiting substance containing at least one basic group and a derivative of the phospholipase A2 inhibiting substance containing at least one acid group.

7. The method of claim 1 wherein the phospholipase A2 inhibitor(s) are selected from the group consisting of a) a compound of the formula

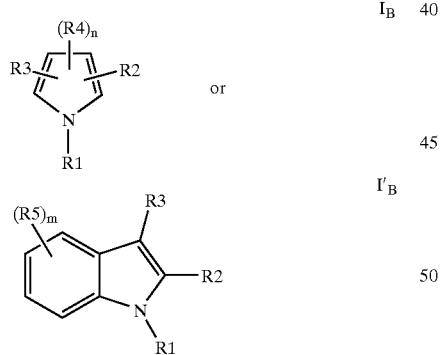

wherein R1 is —Y1-Ar—Y2-Y3 wherein Y1 and Y2 are individually selected from the group consisting of (C$_1$–C$_{12}$)-alkyl, (C$_2$–C$_{12}$)-alkenyl, (C$_1$–C$_{12}$)-alkoxy and (C$_1$–C$_{12}$)-alkenyloxy, Y1 and Y2 are optionally interrupted by at least one oxygen atom, Ar is aryl unsubstituted or substituted with 1 to 3 substituents selected from the group consisting of R6, R7 and R8, and Y3 is selected from the group consisting of —COOR17, —CONR17R17, —CONHCOR19, —CONHS(O)$_2$R19, —CONHNHS(O)$_2$R19 and Tz;

R2 is selected from the group consisting of —COOR17, —Y4-COOR17, —CONR17R17, —Y4-CONR17R17, —CONHCOR19, —Y4-CONHCOR19, —CONHS(O$_2$)R19, —Y4-CONHS(O)$_2$R19, 9-CONHNHS(O)$_2$R19, —Y4-CONHNHS(O)$_2$R19, Tz and —Y4-Tz, Y4 is (C$_1$–C$_8$)-alkyl or (C$_2$–C$_8$)-alkenyl with Y4 optionally interrupted by at least one oxygen atom;

R3 is —CO—R9 wherein R9 is selected from the group consisting of —Y5, aryl and —Y5-aryl, Y5 is selected from the group consisting of (C$_1$–C$_{19}$)-alkyl, (C$_2$–C$_{19}$)-alkenyl and (C$_2$–C$_{19}$)-alkynyl, Y5 is selected from the group consisting of (C$_1$–C$_{19}$)-alkyl, (C$_2$–C$_{19}$)-alkenyl and (C$_2$–C$_{19}$)-alkynyl, Y5 is optionally interrupted by at least one oxygen atom and aryl of R9 being unsubstituted or substituted with 1 to 3 substituents by a member selected from the group consisting of R10, R11 and R12;

each R4 is individually selected from the group consisting of hydrogen, halogen, —CF$_3$, —Y6, aryl and —Y6-aryl, Y6 is selected from the group consisting of (C$_1$–C$_8$)-alkyl, (C$_2$–C$_8$)-alkenyl and (C$_2$–C$_8$)-alkynyl, Y5 is optionally interrupted by at least one oxygen atom and aryl of R4 is unsubstituted or substituted with 1 to 3 substituents individually selected from the group consisting of R13, R14 and R15 and two neighboring Y6 alkyls are able to form together with the carbon atoms to which they are attached a ring with 5 to 8 members optionally substituted by one or two (C$_1$–C$_4$)-alkyls;

n is 2 and m is 4;

Tz is 1H- or 2H-tetrazol-5-yl;

R6, R7, R8, R10, R11, R12, R13, R14, R15 and R16 are individually selected from the group consisting of (C$_1$–C$_{20}$)-alkyl, (C$_2$–C$_{20}$)-alkenyl and (C$_2$–C$_{20}$)-alkynyl optionally interrupted by at least one oxygen atom, halogen, —CF$_3$, —CN, —NO$_2$, —CN, —NO$_2$, —COCH$_2$OH, perhalo(C$_1$–C$_6$)-alkenyl, —OR17, —SR17, —COOR17, —COR18, —NHCOR17, —NR17R17, —NHS(O)$_2$R17, —SOR17, —S(O)$_2$R17, —CONR17R17, —S(O$_2$)NR17R17, —OOCR18, —OOCNR17R17, —OOCOR17, —(CH$_2$)$_r$OR23, —(CH$_2$)$_r$SR23, —(CH$_2$)$_r$NHR23 and —(CH$_2$)$_s$R20;

R17 is, independently each time it occurs, selected from the group consisting of —(CH$_2$)$_r$R20, (C$_1$–C$_{20}$)-alkyl, (C$_2$–C$_{20}$)-alkenyl and (C$_2$–C$_{20}$)-alkynyl optionally interrupted by at least one oxygen atom;

R18 is, independently each time it occurs, selected from the group consisting of R17, —CF$_3$,—(CH$_2$)$_u$COOH and —(CH$_2$)$_u$COOR21;

R19 is, independently each time it occurs, R17 or —CF$_3$;

R20 is, independently each time it occurs, aryl substituted by one or two R22s;

R21 is, independently each time it occurs, selected from the group consisting of (C$_1$–C$_6$)-alkyl, benzyl or phenyl;

R22 is, independently each time it occurs, selected from the group consisting of hydrogen, halogen, (C$_1$–C$_{22}$)-alkyl, (C$_1$–C$_{12}$)-alkoxy, (C$_1$–C$_{12}$)-alkylthio, (C$_1$–C$_{12}$)-alkylsulfonyl, (C$_1$–C$_{12}$)-alkylcarbonyl, —CF$_3$, —CN and —NO$_2$;

R23 is, independently each time it occurs, hydrogen or —COR21;

r is an integer from 1 to 20;

s and t are independently integers from 0 to 12;

and u is an integer from 0 to 4;

b) a compound of the formula

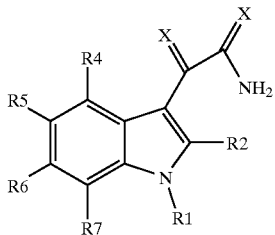

wherein both Xs are oxygen;
R1 is selected from the group consisting of

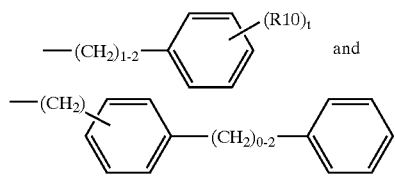

wherein R10 is independently is selected from the group consisting of halogen, $(C_1-C_{10})$-alkyl, $(C_1-C_{10})$-alkoxy, $(C_1-C_{10})$-alkylthio and $(C_1-C_{10})$-haloalkyl and t is an integer from 0 to 5;

R2 is selected from the group consisting of halogen, cyclopropyl, methyl, ethyl and propyl;

R4 and R5 are selected from the group consisting of hydrogen, a substituent which does not interfere and (acid)-$L_a$-(acid group), it being understood that —$L_a$— for R4 is selected from the group consisting of —O—CH$_2$—, —S—CH$_2$—, —NH—CH$_2$, —CH$_2$—CH$_2$—, —O—CH(CH$_3$)— and —O—CH(CH$_2$—CH$_2$—Ph)—, Ph is phenyl and that —$L_a$— for R5 is selected from the group consisting of

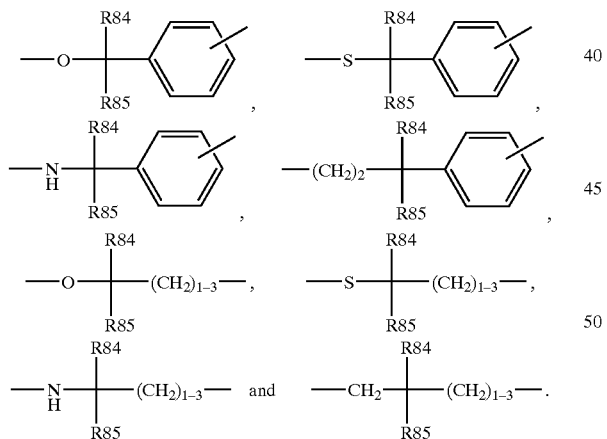

wherein R84 and R85 are individually selected from the group consisting of hydrogen, halogen, $(C_1-C_{10})$-alkyl, aryl, $(C_1-C_{10})$-alkaryl, $(C_1-C_{20})$-aralkyl, carboxy and carbalkoxy, it being understood also that at least one of R4 and R5 must be the —$L_a$-(acid group) and that the (acid group) of R4 and R5 is selected from —CO$_2$H, —SO$_3$H and —P(O)(OH)$_2$;

R6 and R7 are individually hydrogen or a substituent which does not interfere;

the substituents which do not interfere being individually selected from the group consisting of $(C_1-C_6)$-alkyl, $(C_2-C_6)$-alkenyl, $(C_2-C_6)$-alkynyl, $(C_7-C_{18})$-aralkyl, $(C_7-C_{18})$-alkaryl, $(C_3-C_8)$-cycloalkyl, $(C_3-C_8)$-cycloalkenyl, phenyl, toluyl, xylenyl, phenylmethyl, $(C_1-C_6)$-alkoxy, $(C_2-C_6)$-alkenyloxy, $(C_2-C_6)$-alkynyloxy, $(C_2-C_{12})$-alkoxyalkyl, $(C_2-C_{12})$-alkoxyalkyloxy, $(C_2-C_{12})$-alkylcarbonylamino, $(C_2-C_{12})$-alkoxyamino, $(C_2-C_{12})$-alkoxyaminocarbonyl, $(C_2-C_{12})$-alkylamino, $(C_1-C_6)$-alkylthio, $(C_2-C_{12})$-alkylthiocarbonyl, $(C_1-C_6)$-alkylsulfinyl, $(C_1-C_6)$-alkylsulfonyl, $(C_2-C_6)$-haloalkoxy, $(C_2-C_6)$-haloalkylsulfonyl, $(C_2-C_6)$-haloalkyl, $(C_1-C_6)$-hydroxyalkyl, —C(O)O($C_1-C_6$)-alkyl), —(CH$_2$)$_n$—O—(($C_1-C_6$)-alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl and $(C_1-C_6)$-alkylcarbonyl, n being an integer from 1 to 8;

c) a compound of the formula

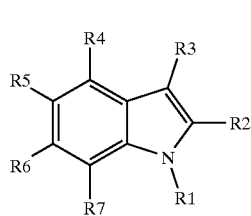

wherein R1 is selected from the group consisting of
(a) $(C_7-C_{20})$-alkyl, $(C_7-C_{20})$-haloalkyl, $(C_7-C_{20})$-alkenyl or $(C_7-C_{20})$-alkynyl, a saturated or unsaturated carbon ring with 5 to 14 members unsubstituted or substituted by at least one substituent which does not interfere, and a saturated or unsaturated heterocycle with 5 to 14 members containing 1 to 3 heteroatoms, unsubstituted or substituted by at least one substituent which does not interfere;
(b) is one (a) substituted by at least one substituent which does not interfere;
(c) represents —(L$_1$)—R11 in which —(L$_1$)— is a member selected from the group consisting of

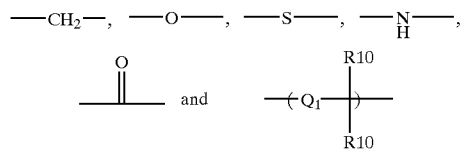

wherein Q$_1$ is selected from the group consisting of a bond, —CH$_2$—, —O—, —S—, —NH— and —CO— and each of R10 is individually selected from the group consisting of hydrogen, $(C_1-C_8)$-alkyl, —($C_1-C_8$)-haloalkyl and $(C_1-C_8)$-alkoxy,
and R11 is a group of (a) or (b);

R2 is selected from the group consisting of hydrogen, halogen, $(C_1-C_4)$-alkyl, $(C_2-C_4)$-alkenyl, —O—$(C_1-C_3)$-alkyl, —S—$(C_1-C_3)$-alkyl, —$(C_1-C_4)$-cycloalkyl, —CF$_3$, —NO$_2$, —CN and —SO$_3$;

R3 is —(L$_3$)—Z in which —(L$_3$)— is selected from the group consisting of a bond, —CH$_2$—, —O—, —S—, —NH— and —CO—;

and 2 is selected from the group consisting of acetamide, thioacetamide, glyoxylamide, thioglioxylamide, hydrazide and thiohydrazide of the formulae

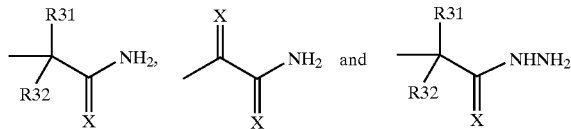

in which R31 and R32 are individually selected from the group consisting of hydrogen, $(C_1-C_8)$-alkyl, $(C_1-C_8)$-haloalkyl and $(C_3-C_4)$-cycloalkyl and X is, independently each time it occurs, oxygen or sulfur;

R4 and R5 are individually selected from the group consisting of hydrogen, a substituent which does not interfere and —$(L_a)$-(acylsulfonamide group) in which —$(L_a)$— for R4 is

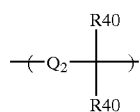

$Q_2$ is selected from the group consisting of —$CH_2$—, —O—, —NH—, —C(O)— and —S—, and each R40 is individually selected from the group consisting of hydrogen, halogen, $(C_1-C_8)$-alkyl, aryl, $(C_1-C_8)$-alkaryl, $(C_1-C_8)$-alkoxy and aralkyl, —$(L_a)$—, $R_5$ is selected from the group consisting of

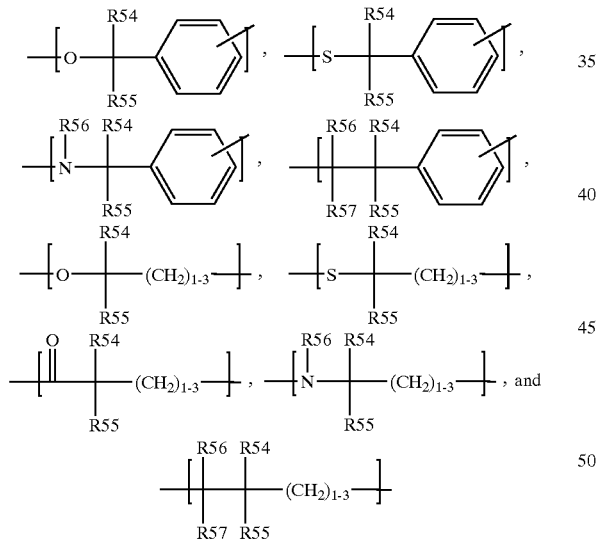

in which R54, R55, R56 and R57 are independently selected from the group consisting of hydrogen, halogen, $(C_1-C_8)$-alkyl, $(C_1-C_8)$-alkoxy, $(C_1-C_8)$-haloalkyl and aryl, the (acylsulfonamide) group being —CO—NH—$SO_2$—R81 wherein R81 is selected from the group consisting of —$CF_3$, $(C_1-C_8)$-alkyl, $(C_1-C_8)$-alkoxy, $(C_1-C_8)$-alkylthio, $(C_1-C_8)$-alkylamino, $(C_1-C_8)$-haloalkyl, $(C_1-C_{14})$-aralkyl, $(C_1-C_{14})$-alkylaryl, aryl, thioaryl, $(C_3-C_{14})$-cycloalkyl and a saturated or unsaturated heterocycle with 3 to 14 members containing 1 to 3 heteroatoms and it being understood, moreover, that at least one of R4 and R5 is an —$(L_a)$-(acylsulfonamide group);

R6 and R7 are individually selected from the group consisting of hydrogen, a substituent which does not interfere, a carbon ring with 5 to 14 saturated or unsaturated members unsubstituted or substituted by at least one substituent which does not interfere or a saturated or unsaturated heterocycle with 5 to 14 members containing 1 to 3 heteroatoms, unsubstituted or substituted by at least one substituent which does not interfere, individually selected from the group consisting of $(C_1-C_8)$-alkyl, $(C_2-C_8)$-alkenyl, $(C_2-C_8)$-alkynyl, $(C_7-C_{12})$-aralkyl, $(C_7-C_{12})$-alkaryl, $(c_3-C_8)$-cycloalkyl, $(C_3-C_8)$-cycloalkyl, $(C_3-C_8)$-cycloalkenyl, phenyl, toluyl, xylenyl, biphenyl, $(C_1-C_8)$-alkoxy, $(C_2-C_8)$-alkenyloxy, $(C_2-C_8)$-alkynyloxy, $(C_2-C_{12})$-alkoxyalkyl, $(C_2-C_{12})$-alkoxyalkyloxy, $(C_2-C_{12})$-alkylcarbonyl, $(C_2-C_{12})$-alkoxyamino, $(C_2-C_{12})$-alkoxyaminocarbonyl, $(C_1-C_{12})$-alkoxyaminocarbonyl, $(C_1-C_{12})$-alkylamino, $(C_1-C_{12})$alkoxyaminocarbonyl, $(C_1-C_{12})$-alkylamino, $(C_1-C_6)$-alkylthio, $(C_2-C_{12})$-alkylthiocarbonyl, $(C_1-C_8)$-alkylsulfinyl, $(C_1-C_8)$-alkylsulfonyl, $(C_2-C_8)$-haloalkoxy, $(C_1-C_8)$-haloalkylsulfonyl, $(C_2-C_8)$-haloalkyl, $(C_1-C_8)$-hydroxyalkyl, —$C(O)O((C_1-C_8)$-alkyl), —$(CH_2)_n$—O—$((C_1-C_8)$-alkyl), benzyloxy, phenoxy, phenylthio, —$CONHSO_2R$, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal and thiocarbonyl, n being an integer from 1 to 8 and R is $(C_1-C_8)$-alkyl; and d) a compound of the formula

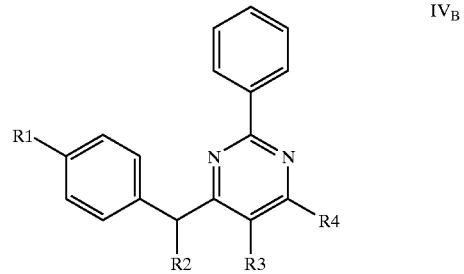

IV$_B$ wherein R1 is selected from the group consisting of halogen, $(C_1-C_6)$-alkyl and $(C_1-C_6)$-alkoxy;

$R_2$ is selected from the group consisting of phenyl or benzyl unsubstituted or substituted on the aromatic ring by a member selected from the group consisting of halogen, $(C_1-C_6)$-alkyl, $(C_1-C_6)$-alkoxy, amino, alkylamino, dialkylamino, carboxyl, carbamoyl, $(C_1-C_8)$-acyl, sulfonyl, thiol or alkylthio, and $(C_3-C_7)$-cycloalkyl optionally condensed with a benzene ring or a heterocycle unsubstituted or substituted by halogen or $(C_1-C_6)$-alkyl;

R3 is selected from the group consisting of halogen and $(C_1-C_6)$-alkyl;

and R4 is selected from the group consisting of —H, —OH, —$N_3$ and —$NHCOCH_3$;

and a pharmaceutically acceptable salt thereof.

8. The method of claim 1 wherein the disorders are selected from the group consisting of atherosclerosis, pulmonary hypertension, glomerulonephritis, portal hypertension, psoriasis, arthrosis and rheumatoid arthritis, fibroses, amyloidoses and inflammation of the gastrointestinal system and the pulmonary system and airways.

9. The method of claim 1 wherein the disorder is selected form the group consisting of lupus, AIDS, parasitic infections, diabetes, multiple sclerosis and myopathies.

10. The method of claim 1 wherein d) Het is selected form the group consisting of oxetane, pyrrole, pyrrolidone, furan, tetrahydrofuran, thiophene, tetrahydrothiopene, sulfolane, piperazine, homopiperazine, 4-aminopiperidineimidazole, imidazoline, dihydroimidazole-2-one, dihydroimidazole-2-thione, oxazole, isoxazole, oxazoline, isoxazoline, oxazolidone, oxazolidinone, thiazole, thiazoline, thiazolidine, thiazolidinone, hydantoin, 1,2,4-triazole, 1,3,4-oxadiazole, 1,3,4-thiadiazole, 1,1-dioxide-1,2,5-thiadiazolidine, 1,2,4-tetrazole-3-one, tetrazole, tetrahydropyridine, azetidine and a pharmaceutically acceptable salt thereof.

11. The method of claim 1 wherein the phospholipase A1 inhibitor(s) are selected from the group consisting of mepacrine, aristolochic acid and their analogues, and the pharmaceutically acceptable salts thereof.

* * * * *